(12) United States Patent  
Leitao et al.

(10) Patent No.: US 12,230,385 B2  
(45) Date of Patent: Feb. 18, 2025

(54) SYSTEMS, METHODS, AND DEVICES FOR ENHANCED DICOM DE-IDENTIFICATION

(71) Applicant: Hyland Software, Inc., Westlake, OH (US)

(72) Inventors: Carlos Leitao, Mississauga (CA); Razvan Atanasiu, Victoria, MN (US)

(73) Assignee: Hyland Software, Inc., Westlake, OH (US)

( * ) Notice: Subject to any disclaimer, the term of this patent is extended or adjusted under 35 U.S.C. 154(b) by 383 days.

(21) Appl. No.: 17/877,155

(22) Filed: Jul. 29, 2022

(65) Prior Publication Data

US 2024/0038363 A1 Feb. 1, 2024

(51) Int. Cl.
*G16H 30/20* (2018.01)
*G06V 30/148* (2022.01)

(52) U.S. Cl.
CPC ........... *G16H 30/20* (2018.01); *G06V 30/153* (2022.01); *G06V 2201/03* (2022.01)

(58) Field of Classification Search
CPC ... G16H 30/20; G06V 2201/03; G06V 30/153

USPC .......................................................... 382/128
See application file for complete search history.

(56) References Cited

U.S. PATENT DOCUMENTS

| 11,615,878 | B2 * | 3/2023 | Accomazzi | G16H 40/20 |
| | | | | 382/128 |
| 11,669,965 | B2 * | 6/2023 | Yao | G06V 10/764 |
| | | | | 382/128 |
| 11,688,495 | B2 * | 6/2023 | De Francesco | G16H 10/60 |
| | | | | 713/182 |
| 2016/0124949 | A1 * | 5/2016 | Chau | G06F 16/00 |
| | | | | 707/665 |
| 2020/0273558 | A1 * | 8/2020 | Yousfi | G16H 15/00 |

* cited by examiner

*Primary Examiner* — Allen H Nguyen
(74) *Attorney, Agent, or Firm* — Eschweiler & Potashnik, LLC

(57) ABSTRACT

Techniques, described herein, enable enhanced de-identification solutions for digital imaging and communications in medicine (DICOM) systems and records. DICOM header tags may be de-identified (e.g., anonymized) using one or more hashing algorithms and salt values. Solutions for evaluating and resolving collisions between de-identified DICOM records may be de-identified in large batches or in smaller batches on a per-request basis. Additional features of the techniques are described herein.

20 Claims, 11 Drawing Sheets

SYSTEMS, METHODS, AND DEVICES FOR ENHANCED DICOM DE-IDENTIFICATION

FIELD

This disclosure relates to computerized networks and data management systems for imaging and communications particularly in the healthcare field.

BACKGROUND

Computerized networks and data management systems may include a variety of systems, devices, and technologies to enable users to create, store, access, and distribute information. Such networks may include one or more wired networks, wireless networks, or a combination thereof. Each network may include a broad range of interconnected devices, each comprising hardware, software, virtualization technology, etc., which enables the devices to send, receive, process, and/or store information. Examples of such devices may include mobile user devices (e.g., cell phones, tablet computers, laptop computers, etc.) stationary devices (e.g., desktop computer, servers, etc.), and network components and devices (e.g., network hubs, routers, base stations, satellite systems, etc.).

Digital imaging and communications in medicine (DI-COM) is a standard used for the communication and management of medical imaging information and related data. DICOM may be used by, for example, hospitals, doctor offices, governments agencies, research institutions, and other types of organizations. DICOM may be implemented for storing and transmitting medical images, enabling the integration of medical imaging devices such as scanners, servers, workstations, printers, network hardware, and picture archiving and communication systems (PACS) from multiple manufacturers.

BRIEF DESCRIPTION OF THE DRAWINGS

The present disclosure will be readily understood and enabled by the detailed description and accompanying figures of the drawings. Like reference numerals may designate like features and structural elements. Figures and corresponding descriptions are provided as non-limiting examples of aspects, implementations, etc., of the present disclosure, and references to "an" or "one" aspect, implementation, etc., may not necessarily refer to the same aspect, implementation, etc., and may mean at least one, one or more, etc.

DETAILED DESCRIPTION

Figure 1:
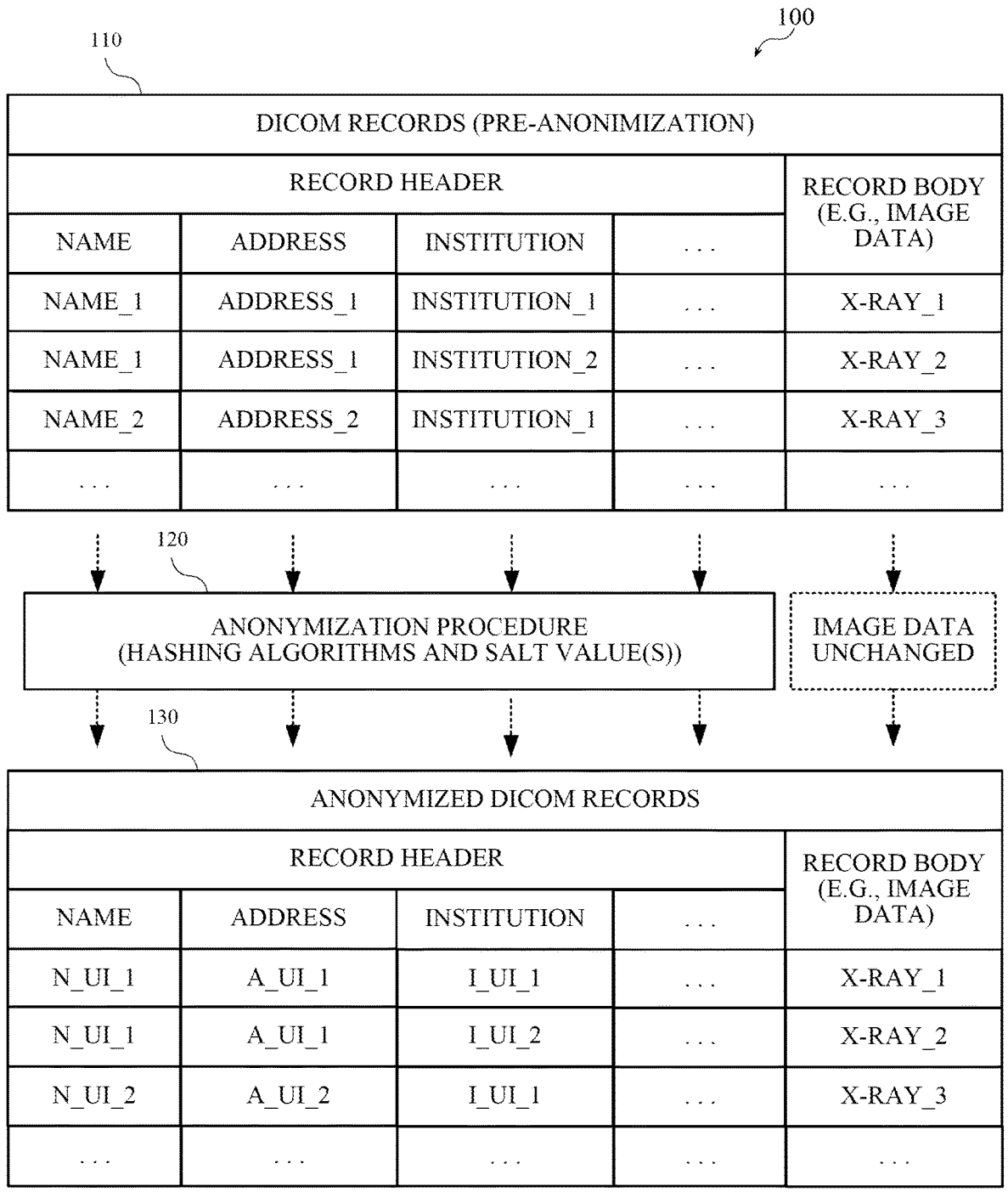
FIG. 1 is a diagram of an example overview according to one or more implementations described herein.

The following detailed description refers to the accompanying drawings. Like reference numbers in different drawings may identify the same or similar features, elements, operations, etc. Additionally, the present disclosure is not limited to the following description as other implementations may be utilized, and structural or logical changes made, without departing from the scope of the present disclosure.

Digital imaging and communications in medicine (DI-COM) is a standard used for the communication and management of medical imaging information and related data. DICOM may be used by, for example, hospitals, doctor offices, governments agencies, research institutions, and other types of organizations. DICOM may be implemented for storing and transmitting medical images, enabling the integration of medical imaging devices such as scanners, servers, workstations, printers, network hardware, and picture archiving and communication systems (PACS) from multiple manufacturers. The DICOM standards describes a format of medical images, as well as their distribution, in terms of a communication protocol. Each DICOM instance may be in a binary format and may consist of a header, which may include a dictionary of key value pairs. A key may also be referred to as a tag, and a tag may have a value representation (VR) type or code, such as a PN (person name), UI (unique identifier), SH (short string), LO (long string), OB (binary data), etc.

A feature of DICOM systems may include data de-identification or anonymization, whereby medical records formatted according to the DICOM standard may be modified by removing identifying information (e.g., patient information, doctor information, hospital information, etc.) while preserving other types of information (e.g., the results of an x-ray, magnetic resonance imaging (MRI) scan, etc.). Generally, a DICOM medical record or file may include a header and a body arranged according to a format specified by the DICOM standards. The header may include a variety of attributes (also referred to as keys, tags, DICOM tags, etc.), some of which may be identifying information. The body may include, for example, the imaging information of the corresponding x-ray, MRI, etc. De-identification or anonymization may include modifying the value of tags in the DICOM header so that the medical record (or DICOM file) may be shared with other organizations, such as data storage companies, research institutions, etc., while preserving an appropriate degree of anonymity.

The quantity of records to be de-identified or anonymized in a given batch or set of records may be large and complex (e.g., involving millions of records, multiple studies, multipole institutions, etc.). As such, an ability to de-identify large sets of medical records efficiently is desirable so long as the processes for doing so does not result in a problematic number of collisions among the processed records. A "collision" as used herein may include a scenario in which two or more medical records with the same value of a given attribute, which collisions with the pre-anonymization records. For example, assume that de-identifying a batch or set of medical records includes changing (e.g., anonymizing) an institution attribute from each records. A de-identification process that involved anonymizing one set of medical records, which included records from different institutions, would create collisions if the institution attribute were changed to the same unique identifier (UI) value. In such a scenario, a research institution (for example) attempting to study the medical records may be frustrated since researcher would be unable to tell which records came from different institutions. As such, systems, methods, and devices capable of efficient de-identification while minimizing collisions is desirable since the resulting records are anonymous but still appraisal unique.

Techniques, described herein, enable enhanced DICOM de-identification solutions. FIG. 1 is a diagram of an example overview 100 according to one or more implementations described herein. As shown, overview 100 may include pre-anonymization DICOM records 110, an anonymization procedure 120, and anonymized DICOM records 130. As described herein, a set of DICOM record may be referred to as a DICOM batch or study, and a DICOM record may be referred to as a DICOM object or instance. Referring to FIG. 1, each pre-anonymization DICOM record 110 may include a record header that includes one or more tags or attributes and a record body. Examples of tags may include patient name (e.g., NAME_1, NAME_2, etc.), patient address (e.g., ADDRESS_1, ADDRESS_2, etc.), institution name (e.g., INSTITUTION_1, INSTITUTION_2, etc.), and more. An example of a record body may include image data (e.g., X-RAY_1, X-RAY_2, etc.).

Pre-anonymization DICOM records 110 may be subjected to anonymization procedure 120. As described herein, this may include applying one or more hashing algorithms and salt values to identification information of the record header of each DICOM record. The result may include anonymized DICOM records 130, which may include the same identifying tags as pre-anonymization DICOM records 110, but without the identifying information. For example, NAME_1 may be changed to a unique identifier (UI) or UI value (UIV) (represented as N_UL1), ADDRESS_1 may be changed to an address UI or UIV (represented as A_UL1), and so on. By contrast, the image data for each DICOM record may remain unchanged. So, for example, X-RAY_1 may still be associated with a set of identifying tag values (e.g., N_UI_1, A_UI_1, and I_UI_1) but the actual identifying information of the pre-anonymization DICOM records 110 (e.g., NAME_1, ADDRESS_1, etc., which may be value representation (VR) types UI)) will have become anonymized as UIVs.

Additionally, as shown, since the same hashing algorithms and salt values may be used for each type of tag (e.g., NAME), the resulting UI value or UIV may be consistent for different records (e.g., NAME_1 may consistently result in N_UL1). Anonymization of DICOM records may therefore ensure the anonymity of identifying information without forfeiting an ability to maintain the logical integrity, accuracy, and interrelationships between DICOM records, tags, and values. In turn, collision between anonymized DICOM records may be kept at a minimum since the functionality of anonymized identifying information is retained for record keeping purposes. Furthermore, since hashing algorithms produce the same output based on the same input, the DICOM anonymization techniques described herein may reduce the computing resources needed for anonymization since large amounts of variables may not need to be stored in memory during the anonymization of large batches of DICOM records. These and other features, including the detection and resolution of collisions, are described below in greater detail with reference to the figures that follow.

Figure 2:
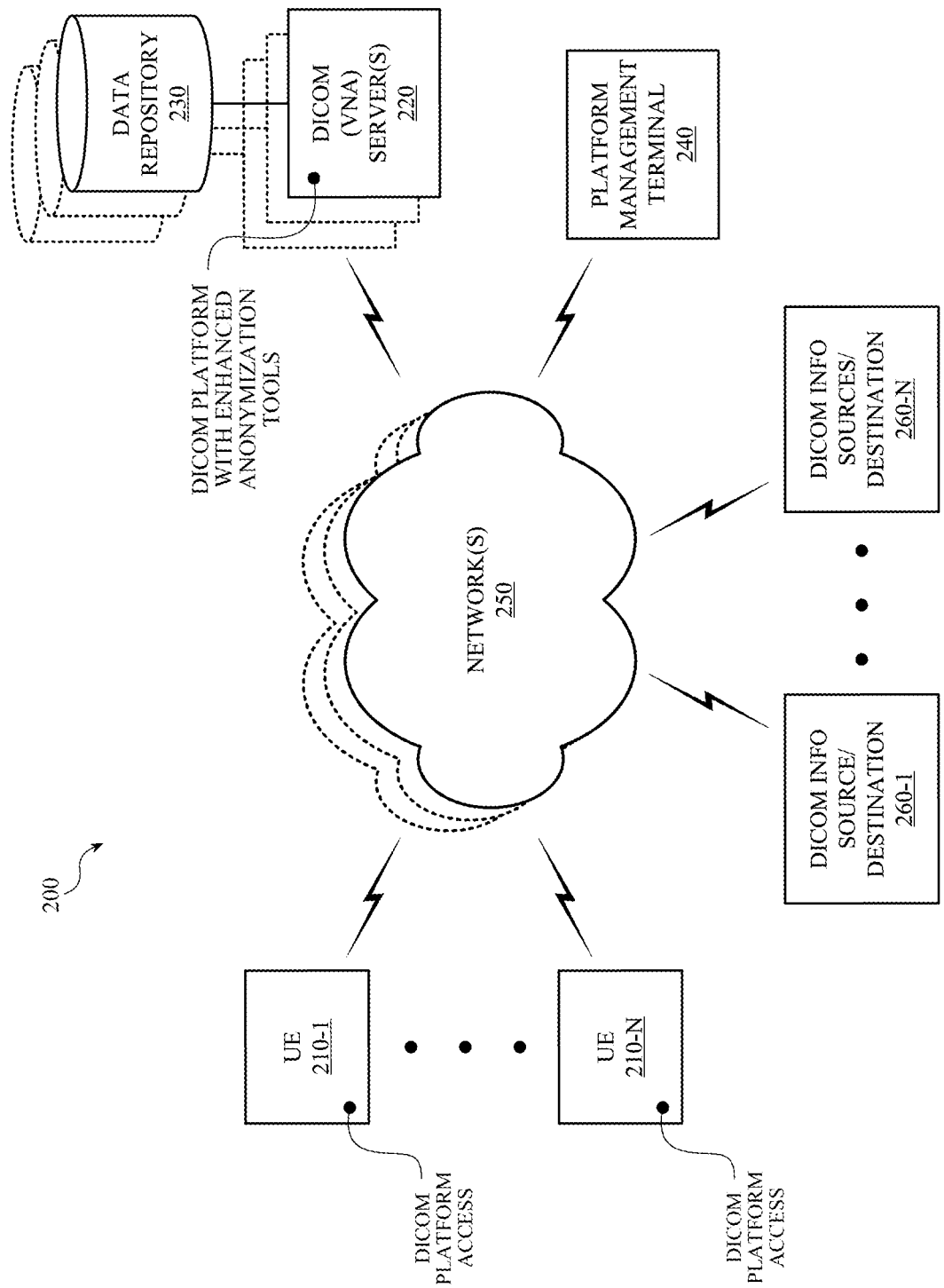
FIG. 2 is a diagram of an example network according to one or more implementations described herein.

FIG. 2 is a diagram of an example environment 200 in which systems and/or methods, described herein, may be implemented. As depicted, environment 200 may include user equipment (UE) 210-1, . . . 210-N (where N is greater than or equal to 2 and collectively referred to as "UEs 210"), DICOM servers 220, data repositories 230, platform management terminal 240, DICOM source/destination 250-1, . . . 250-M (where N is greater than or equal to 2 and collectively referred to as "DICOM sources/destinations 250"), and network 250. The number of devices and/or network, illustrated in FIG. 2, is provided for explanatory purposes only. In practice, there may be additional devices and/or networks, fewer devices and/or networks, different devices and/or networks, or differently arranged devices and/or networks than illustrated in FIG. 2. Devices of environment 200 may interconnect via wired connections, wireless connections, or a combination of wired and wireless connections. Also, in some implementations, one or more of the devices of environment 200 may perform one or more functions described as being performed by another one or more of the devices of environment 200.

UE 210 may include any type computing device, such as a wired or wireless user device, that is capable of communicating with network 250. For example, UE 210 may include a smartphone, tablet computer, laptop computer, wearable device, etc. UE 210 may alternatively include a desktop computer, a radiotelephone, a personal communications system (PCS) terminal (e.g., that may combine a cellular radiotelephone with data processing and data communications capabilities), a personal digital assistant (PDA) (e.g., that can include a radiotelephone, a pager, Internet/intranet access, etc.), or another type of computation or communication device. UE 210 may include any variety of peripheral devices, such as speaker, cameras, external storage devices, etc. UE 210 may include a browser or another type of application or interface capable of accessing a DICOM platform hosted by DICOM servers 220.

DICOM servers 220 may include one or more servers or other types of computing devices capable of gathering, processing, searching for, storing, and/or communication information as described herein. In some implementation, DICOM servers 220 may include an application server or a web server that stores one or more applications and/or that permits the one or more applications to be accessed and/or downloaded by UEs 210. DICOM servers 220 may include a single server device, group of server devices, and/or one or more virtual servers. In some implementations, DICOM servers 220 may comprise a DICOM platform as described herein. The DICOM platform may operate, in accordance with DICOM standards, to receive, store, process, secure, and/or provide DICOM information. The DICOM platform may also, or alternatively, include one or more tools, features, or processes capable of perform some or all of the de-identification or anonymization techniques described herein. In some implementations, DICOM servers 220, in combination with one or more other types of devices, e.g., UEs 210, data repositories 230, platform management terminals 240, etc., may comprise a DICOM platform. In some implementations, DICOM servers 220 may include a vendor neutral achieve (VNA) system capable of receiving and storing DICOM information and other types of data from a variety of sources, such as research instructions, hospitals, doctor offices, etc. In some implementations, DICOM servers 220 may also, or alternatively, be connected to a VCN system and may retrieve DICOM studies and objects from the VCN system for anonymization processing as described herein.

Data repositories 230 may include one or more data storage devices capable of receiving, storing, and providing data related to DICOM information, the management and processing of DICOM information, etc. In some implementations, data repositories 230 may include a database or another type of data storage system or framework for organizing and storing data. In some implementations, DICOM servers 220 and data repository 230 may be connected via network 250. Platform management terminal 240 may include any type of wired or wireless user device capable of communicating with DICOM servers 220 and/or data repositories 230 via network 250. Platform management terminal 240 may include a smartphone, tablet computer, laptop computer, desktop computer, or another type of user device capable of enabling a user, operator, administrator, or developer to interact with DICOM servers 220 and/or the DICOM platform. In some implementations, platform management terminal 240 may be a UE 210. Additionally, or alternatively, platform management terminal 240 may be directly connected to DICOM servers 220. In some implementations, data repositories 230 may be, or may be part of, a VCN system.

DICOM sources/destinations 250 may include one or more computing devices, such as a user devices, network devices, and/or server device capable of receiving, processing, storing, and communicating information via network 250. DICOM sources/destinations 250 may be owned or operated by a particular institution (e.g., a doctor's office, hospital, research institution, government agency, records archive, etc.). DICOM sources/destinations 250 may be capable of creating and sending DICOM information (e.g., DICOM studies, DICOM objects, etc.) to DICOM servers 220 for processing and/or storage. Additionally, or alternatively, DICOM sources/destinations 250 may request and receive DICOM information from DICOM servers 220 and/or form another DICOM source/destination. In some implementations, DICOM sources/destinations 250 a VCN system capable of receiving, storing, and distributing DICOM information to DICOM servers 220 and/or other DICOM sources/destinations 250.

Network 250 may include a single network or multiple networks capable of enabling a connection between the devices of FIG. 2. Network 250 may include one or more wired and/or wireless networks. For example, network 250 may include a Bluetooth® network, a Wi-Fi network, or a cellular network, the Public Land Mobile Network (PLMN), and/or a second generation (2G) network, a third generation (3G) network, a fourth generation (4G) network, a fifth generation (5G) network, a sixth generation (6G) network and/or another type of network. Additionally, or alternatively, network 250 may include a wide area network (WAN), a metropolitan area network (MAN), an ad hoc network, an intranet, the Internet, a virtual network (e.g., a virtual private network (VPN)), a telephone network (e.g., a Public Switched Telephone Network (PSTN)), a Voice over IP (VoIP) network, and/or a combination of these or other types of networks.

Figure 3:
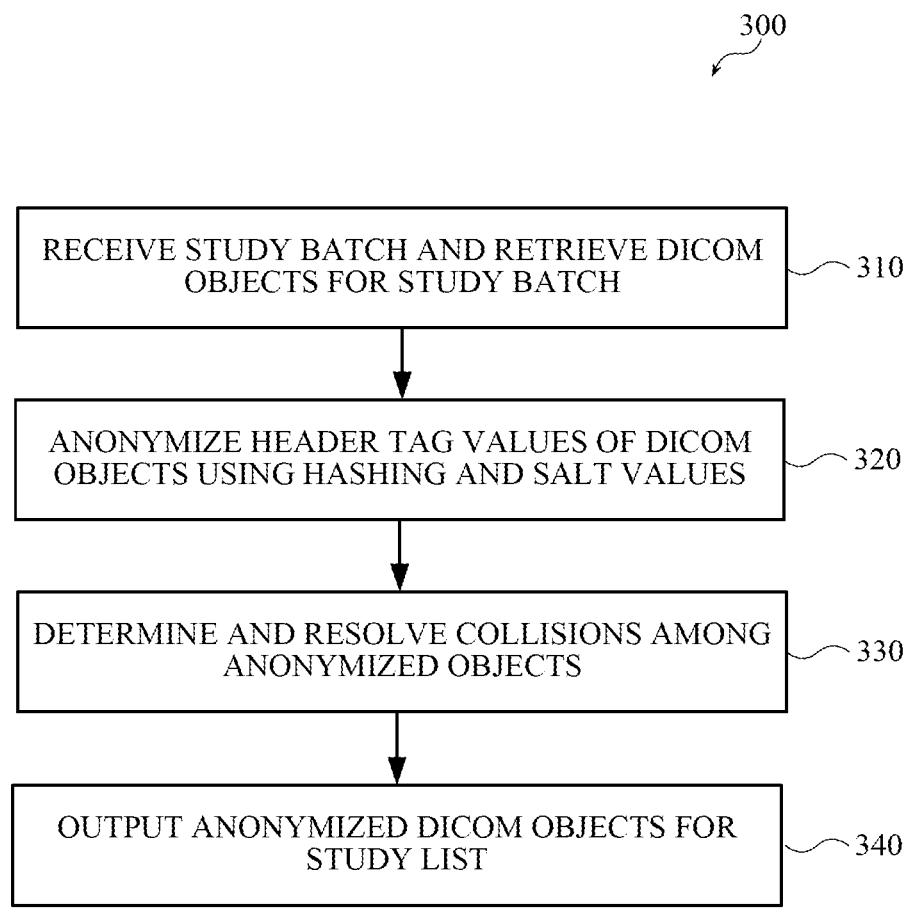
FIG. 3 is a diagram of an example process for de-identifying DICOM records according to one or more implementations described herein.

FIG. 3 is a diagram of an example process 300 for de-identifying DICOM records according to one or more implementations described herein. Process 300 may be implemented by one or more DICOM servers 220. In some implementations, some or all of process 300 may be performed by one or more other systems or devices, including one or more of the devices of FIG. 2. Additionally, process 300 may include one or more fewer, additional, differently ordered and/or arranged operations than those shown in FIG. 3 and may be implemented within the context of a variety of other processes involving different devices. For example, in some implementations, process 300 may include checking for collisions before anonymizing DICOM records instead or, or in addition to, doing so afterwards.

In some implementations, some or all of the operations of process 300 may be performed independently, successively, simultaneously, etc., of one or more of the other operations of process 300. For example, process 300 may involve include DICOM servers 220 receiving commands or other types of inputs from UE 210, performing one or more operations of process 300, and providing UE 210 with corresponding results or outputs. In some implementations, process 300 may involve include UE 210 requesting and receiving a DICOM study batch from DICOM servers 220, UE 210 anonymizing certain header tags of the DICOM study batch and providing the anonymized DICOM study batch to DICOM servers 220 and/or to another type of computing device, such as DICOM sources/destinations 250.

In some implementations, DICOM sources/destinations 250 may send a request to UE 210 for an anonymized DICOM study batch, UE 210 may communicate with DICOM servers 220 to access (from data repository 230) the DICOM study batch and to anonymize the DICOM study batch and inform DICOM sources/destinations 250 when the anonymization is complete so that DICOM sources/destinations 250 may retrieve the anonymized DICOM study batch from DICOM servers 220. As such, the techniques described herein are not limited to a number, sequence, arrangement, timing, etc., of the operations or process depicted in FIG. 3 Process 300 is described below with periodic reference to FIGS. 4-9.

As shown, process 300 may include receiving a study batch and retrieving DICOM objects for the study batch (block 310). For example, DICOM servers 220 may receive a request from UE 210 to anonymize a DICOM study batch that includes one or more DICOM objects (also referred to as DICOM records, DICOM instances, etc.). The request for the DICOM study batch may indicate the DICOM objects included in the study. This may be done based on one or more parameters, or combinations of parameters, such as DICOM objects between certain date ranges, associated with a particular hospital or other institution, one or more patient attributes (e.g., name, age, gender, city, state, etc.), one or more type of image data (e.g., x-ray, magnetic resonance imaging (MRI) scan, etc.), one or more DICOM object UIs, etc. DICOM servers 220 may retrieve the DICOM objects for the study, based on the request, from data repository 230.

Figure 4:
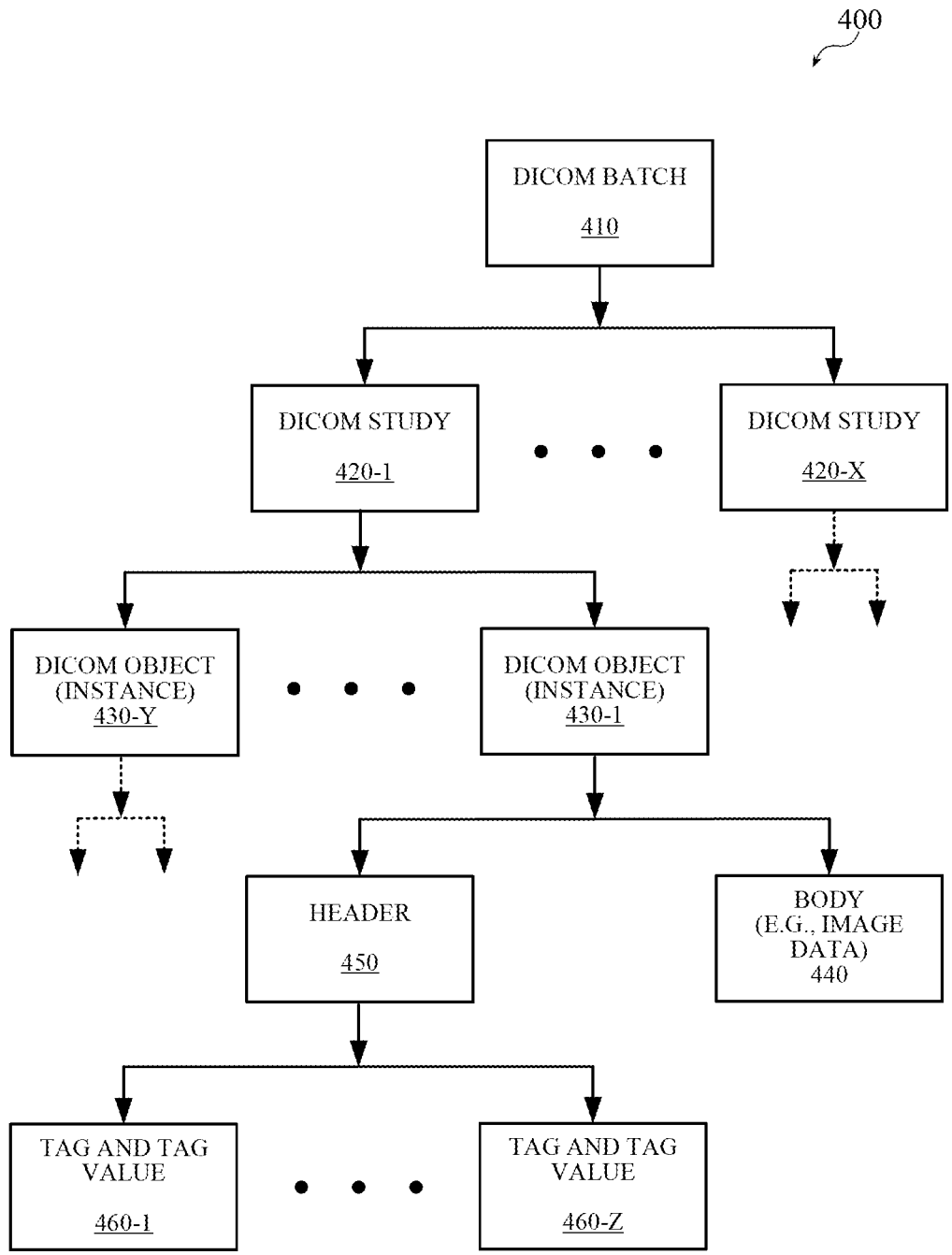
FIG. 4 is a diagram of an example of a data structure of a study batch of DICOM objects according to one or more implementations described herein.

FIG. 4 is a diagram of an example of a data structure 400 of a study batch of DICOM objects according to one or more implementations described herein. As shown, a DICOM batch 410 may include one or more DICOM studies 420-1, . . . 420-X (where X is greater than or equal to 2), and each DICOM study 420 may include one or more DICOM objects 430-1, . . . 430-Y where Y is greater than or equal to 2). A DICOM object may be referred to as a DICOM instance, and a DICOM object may be implemented as a data file that includes a body 440 (e.g., an x-ray image or another type of image data) and header 450. The header 450 may include multiple tags (also referred to as keys or attributes) and corresponding tag values 460-1, . . . 460-Z (where Z is greater than or equal to 2).

The tags may be specified by the DICOM standards. Examples of tag types may include a patient name, patient age, patent race, patient gender, patient address, patient contact information, patient ID, medical record number (MRN), date when the DICOM object was created, a time when the DICOM object was created, institution where the DICOM object was created, study ID, study instance ID, series instance ID, etc. In some implementations, the values of one or more tags may be a unique identifier (UI). As such, the size of a DICOM batch 410 may vary in size by including one or more DICOM studies 420, which each DICOM study 420 include one or more DICOM objects 430 associated with the study. In some implementations, a DICOM batch 410 may include a single DICOM study 420 and DICOM object 430. In some scenarios, a DICOM batch 410 may include many DICOM studies 420, each with many DICOM objects 430. Techniques, described herein may be used to de-identify or anonymize the DICOM batch by, for example, determining types of header tags to be anonymized, applying a hashing function and salt value to the header tags, and replacing the tag value with the output of the hashing function.

Figure 5:
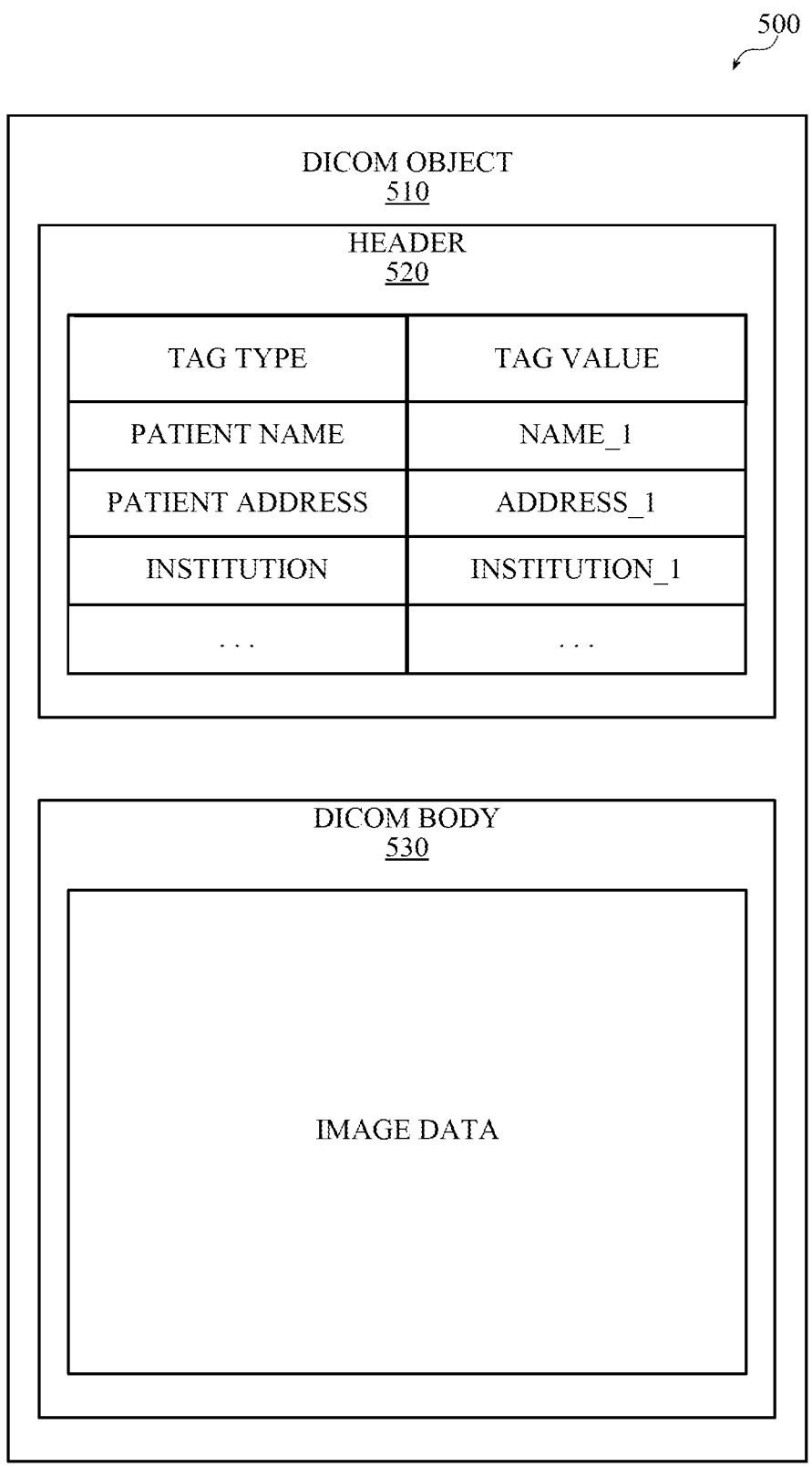
FIG. 5 is a diagram of an example of a DICOM object 500 according to one or more implementations described herein.

FIG. 5 is a diagram of an example 500 of a DICOM object 510 according to one or more implementations described herein. As shown, DICOM object 510 include a header 520 and DICOM body 530. Header 520 may include multiple keys or tags (e.g., patient name, patient address, instruction, etc. Each type of tag may include a corresponding value, such as NAME_1, ADDRESS_1, INSTITUTION_1, etc. DICOM body 530 may include one or more images, or another type of medical information, associated with DICOM object 510. Examples of DICOM body 530 may include an x-ray image, an MRI, and/or one or more other types of images or medical records.

Referring to FIG. 3, process 300 may also include anonymizing header tag values of DICOM objects using hashing algorithms and salt values (block 320). For example, DICOM servers 220 may identify target tags in headers of the DICOM objects and anonymize the values corresponding to the tags by apply one or more hashing algorithms and salt values. In some implementations, anonymization rules or instructions may be applied such that only certain tags, or certain types of tags, may be anonymized. In some implementations, different hashing functions may be used for different types of types of header tags. Additionally, or alternatively, a different or unique salt value may be used for each type of hashing function and/or study batch. The instructions may be received or selected by UE 210. Alternatively, the instructions may be identified by DICOM servers 220 based on another condition, such as a type, quantity, category, etc., of the DICOM objects, a stated purpose for the record request, a user, institution, or organization indicated as requesting the DICOM study batch, etc. In some implementations, DICOM servers 220 may be configured to anonymize one or more types of header tags, such as identification tags, unique identification tags, etc.

DICOM servers 220 may obtain the requested DICOM objects, determine which types of tags are to be anonymized, identify the tags in each DICOM object header, and proceed to anonymize the value of the identified tags. This may include DICOM servers 220 using the value of the tag (or a combination or concatenation of the value of several tags) as an input to one or more hashing functions and salt values to produce a corresponding output that is unique yet anonymizes the input value. As DICOM servers 220 may use the same hashing function and salt value to anonymize the same type of tag (e.g., patient name) for each DICOM object of the DICOM study batch, DICOM servers 220 may not be encumbered by storing a record of which input value was linked to which output value since the same hashing function and salt value will ensure that the same input value results in the same output value. In this manner, the data integrity and consistency between DICOM objects may be preserved.

Figure 6:
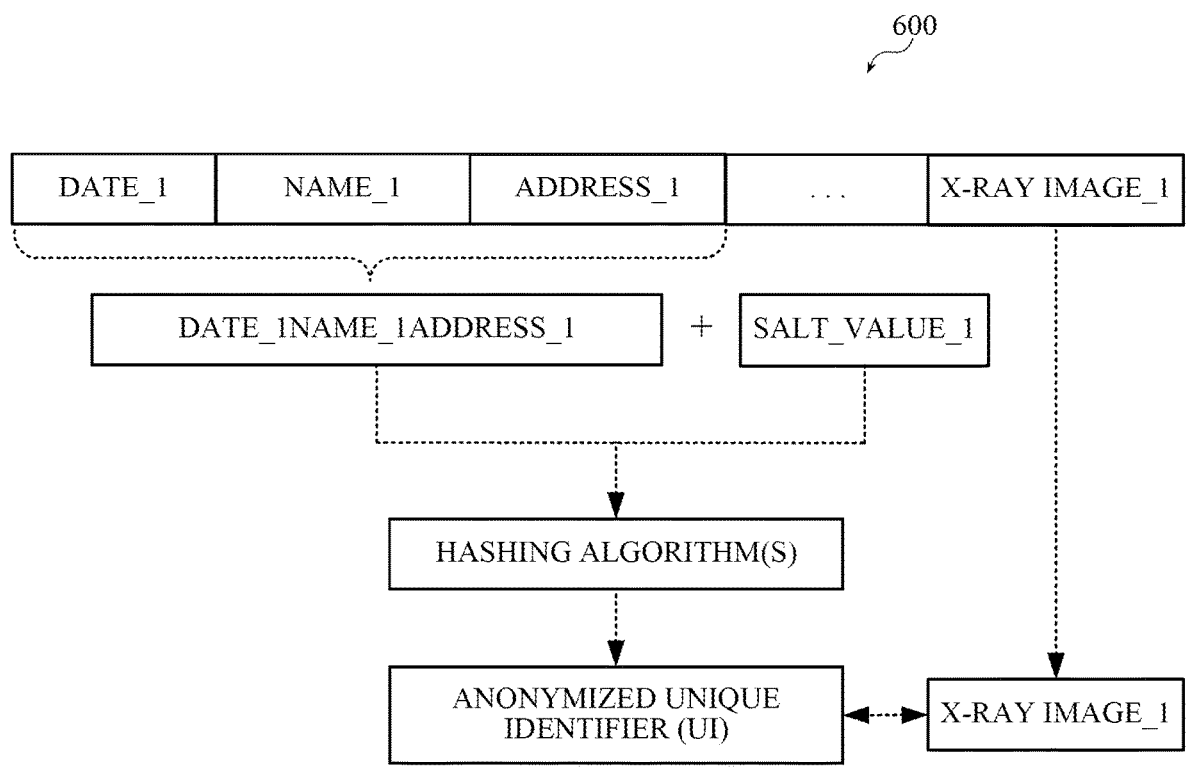
FIG. 6 is a diagram of an example of de-identifying a unique identifier (UI) of a name tag of a DICOM object according to one or more implementations described herein.

FIG. 6 is a diagram of an example 600 of de-identifying a unique identifier (UI) of a name tag of a DICOM object according to one or more implementations described herein. As shown, several tag attributes. In the depicted example, the values for the tags: date, name, and address may be combined to create a UI (DATE_1NAME_1ADDRESS_1). A salt value (SALT_VALUE_1) may be combined with the UI as used as an input for one or more hashing algorithms 610 to generate an anonymized UI, and the anonymized UI may be used as a header tag value for the DICOM object that include an x-ray image (X-RAY IMAGE_1).

Referring to FIG. 3, process 300 may include determining and resolving collisions among anonymized DICOM objects (block 330). For example, DICOM servers 220 may analyze a batch of DICOM studies to determine whether there are collisions between anonymized DICOM objects. In some implementations, DICOM servers 220 may also, or alternatively, analyze a batch of DICOM studies and/or objects prior to anonymizing header tag values of DICOM objects. In some implementations, this may help ensure that taking the time and resources to perform an entire anonymization procedure would not result in any collisions or would only result in a manageable number of collisions.

A collision may include a scenario in which anonymized tag values (e.g., a patient ID) for different DICOM objects (e.g., from different DICOM studies) end up being the same when they should be different, and therefore create confusion as to which DICOM objects pertain to which DICOM objects, studies, batches, etc. For example, if different people went to different hospitals but ended up having the same patient IDs, a collision may arise if the patient IDs were each input into the same hashing function because it would result in the same output value and therefore make it appear as though each DICOM object corresponds to the same person even though they do not.

DICOM servers 220 may identify collisions by comparing pre-anonymized tag values DICOM objects with anonymized tag values of DICOM objects. In some implementations, DICOM servers 220 may efficiently identify collisions by selectively comparing tag values that have been anonymized instead of, for example, all the tag values of all DICOM objects of a DICOM batch or study. This may be because not all DICOM objects, of a DICOM batch or study, may undergo anonymization, and/or because not all tag values of DICOM objects may undergo anonymization. As such, DICOM servers 220 may reduce the resources used to identify collisions and expedite the overall anonymization process by focusing on relevant DICOM objects and/or tag values. DICOM servers 220 may also, or alternatively, resolve collisions. In some implementations, DICOM servers 220 may resolve collisions by implementing one or more rules pre-emptively (before anonymizing header tags) and/or retroactively (after anonymizing header tags). Retroactively resolving collisions may include rolling back the anonymization of one or more header tag values, modifying an input value, a salt value, etc., and reapplying the hash functions to produce a corrective output.

In some implementations, DICOM servers 220 may avoid or resolve a collision by adding, editing, or deleting one or more portions of the value of a tag prior to anonymization processing. For example, in a scenario where a DICOM batch includes studies from multiple institutions, it may be possible that applying the same hashing functions and salt values to a particular tag type for all objects in the batch could create collisions. As such, DICOM servers 220 may be configured to add, edit, or delete information from the input or the output of a hashing function. For example, assume the for objects pertaining to Institution ABC, DICOM servers 220 may add the letters ABC to hashing function input (e.g., add the prefix "ABC" to each patient name) so that all of the outputs from the objects pertaining to Institution ABC are distinguishable from the outputs of another research institution (e.g., Institution XYZ). That is, the output for the patient name "Brian" of Institution ABC will be different than the output for "Brian" of Institution XYZ because the hashing function input for "Brian" of Institution ABC would be "ABCBrian" while for "Brian" of Institution XYZ may be "Brian" or perhaps "XYZBrian." In this manner, DICOM servers 220 may avoid collisions and confusion, but still achieve anonymization and inter-record consistency, by modifying hashing function inputs.

Figure 7:
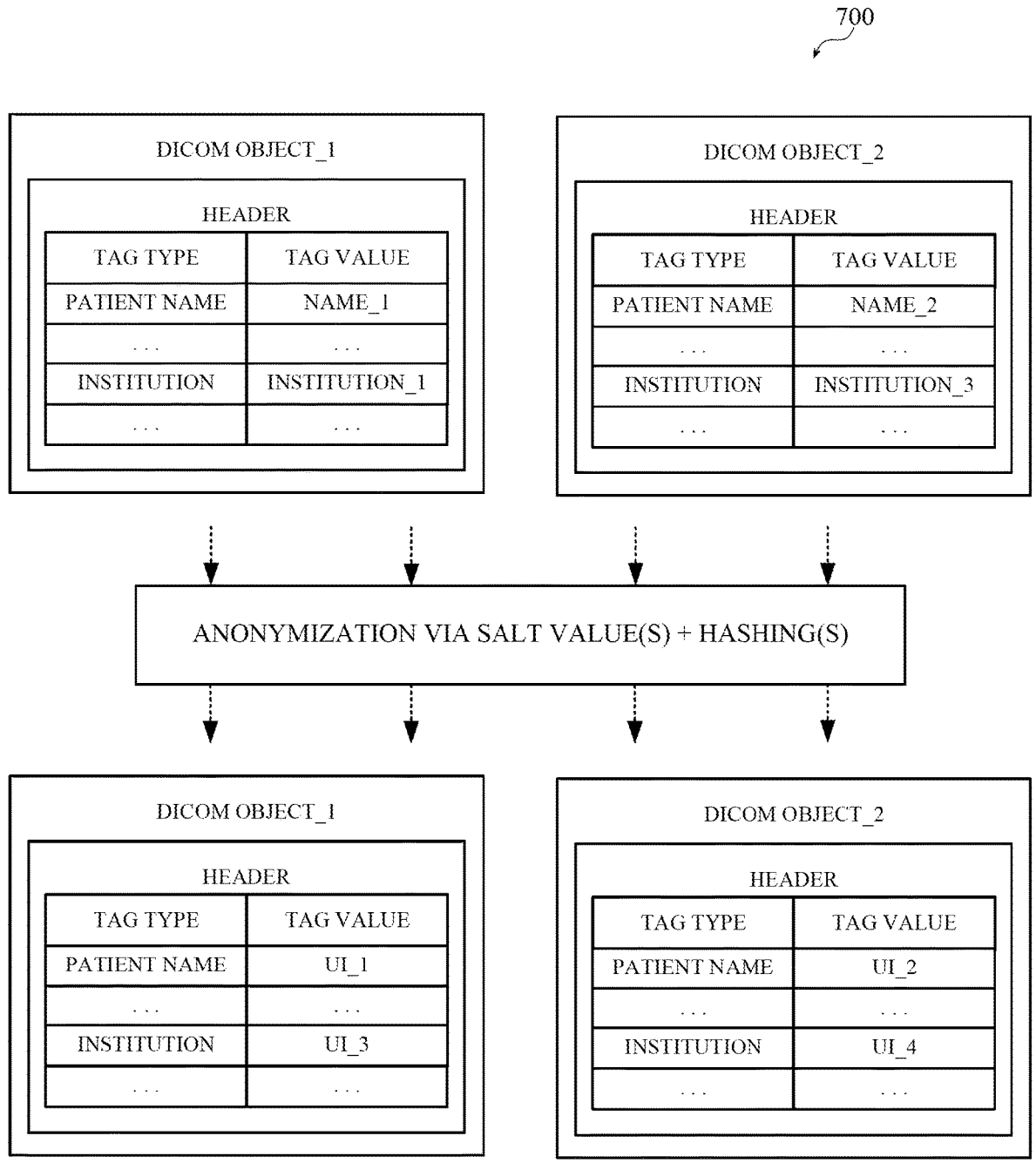
FIG. 7 is a diagram of an example of de-identifying different DICOM objects according to one or more implementations described herein.

FIG. 7 is a diagram of an example 700 of de-identifying different DICOM objects according to one or more implementations described herein. As shown, DICOM object 1 and DICOM object 2 may each include a header with several tags, such as patient name, institution, etc. DICOM object 1 and DICOM object 2 may also include a body (e.g., an image) though not shown. In example 700, hashing functions add salt values may be used to convert tag values into anonymized UIs. As shown, the tag value NAME_1 is converted into UI_1, INSTITUTION_1 is converted into UI_3, and the tag value NAME_2 is converted into UI_2, INSTITUTION_3 is converted into UI_4.

Figure 8:
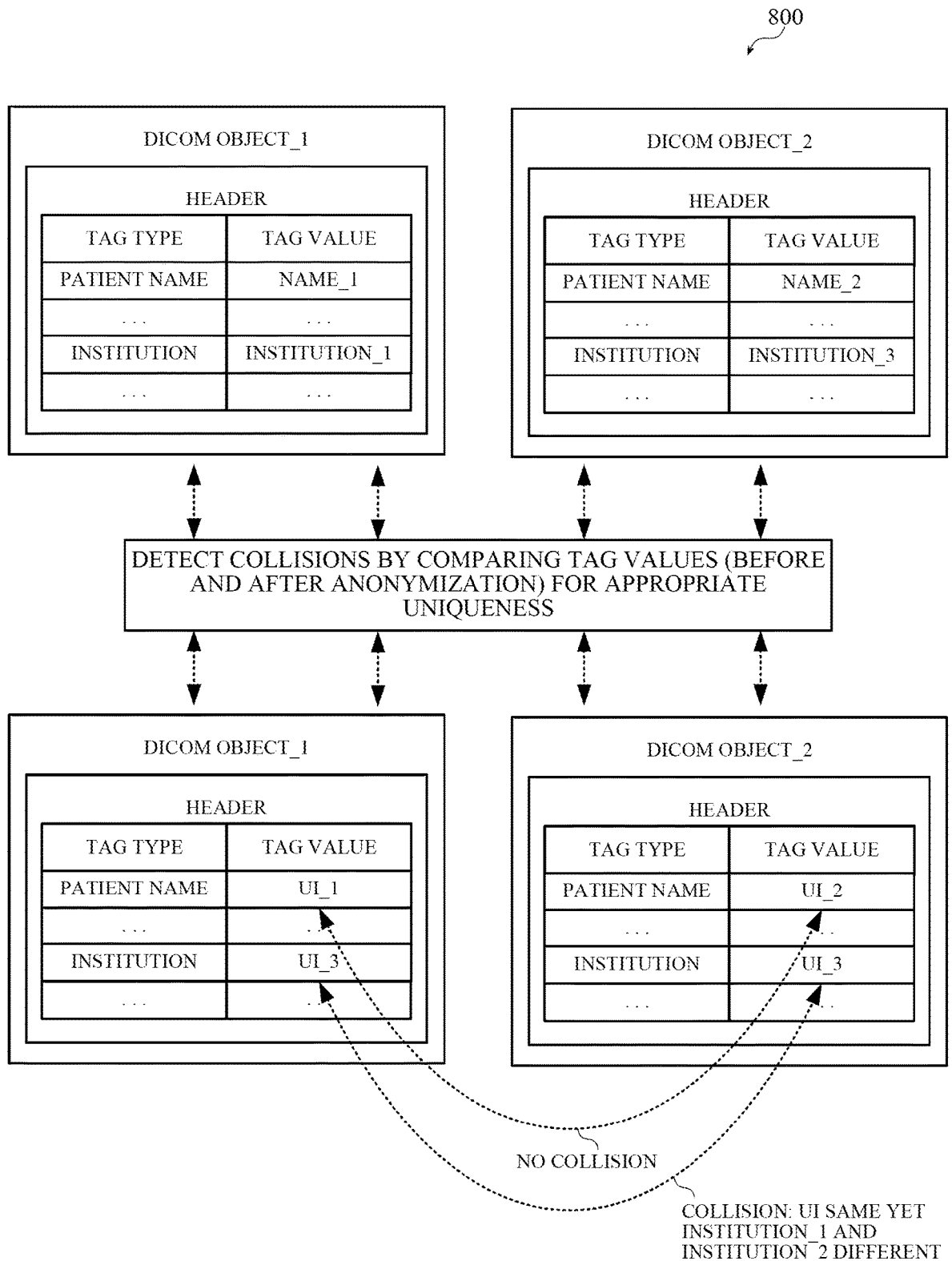
FIG. 8 is a diagram of an example of discovering a collision between de-identified DICOM objects according to one or more implementations described herein.
Figure 9:
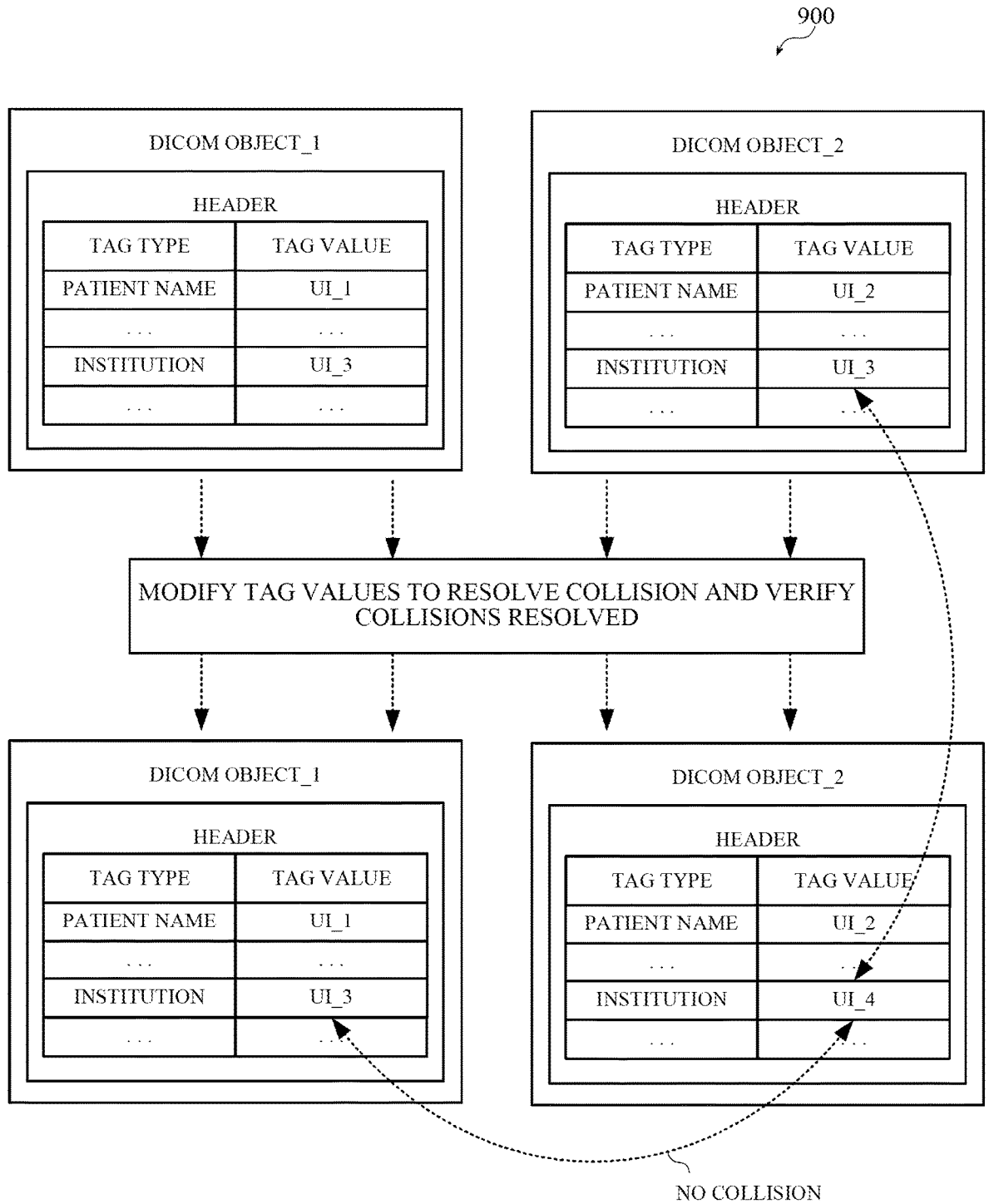
FIG. 9 is a diagram of an example of resolving a collision between de-identified DICOM objects according to one or more implementations described herein.

FIGS. 8 and 9 are diagrams of an example of discovering and resolving a collision between de-identified DICOM objects according to one or more implementations described herein. As shown, DICOM object 1 and DICOM object 2 may each include a header with several tags, such as patient name, institution, etc. DICOM object 1 and DICOM object 2 may also include a body (e.g., an image) though not shown. In example 700, hashing functions add salt values may be used to convert tag values into anonymized UIs. As shown, the tag value NAME_1 is converted into UI_1, INSTITUTION_1 is converted into UI_3, and the tag value NAME_2 is converted into UI_2, INSTITUTION_3 is also converted into UI_3. DICOM object 1 and DICOM object 2 may be compared to determine whether collisions exist, and upon doing so it may be discovered that even though INSTITUTION_1 and INSTITUTION_2 are differ met values, there is a collision because they have both been converted to the same UI value. Referring to FIG. 9, the collision may be resolved by modifying the UI values for INSTITUTION_1 and INSTITUTION_2 so that they are different. In some implementations, this may be done by adding characters to INSTIUTION_2 and re-running the hashing function.

Referring to FIG. 3, process 300 may include outputting anonymized DICOM objects for the study batch (block 340). For example, DICOM servers 220 may produce the anonymized DICOM objects of the study batch. In some implementations, this may include sending a message, posting a link, creating and hosting a file structure, etc., to enable another device to access and download the anonymized DICOM objects. In some implementations, this may also, or alternatively, including storing the anonymized DICOM objects as a study batch in data repository 230, a VNA, or another location.

Figure 10:
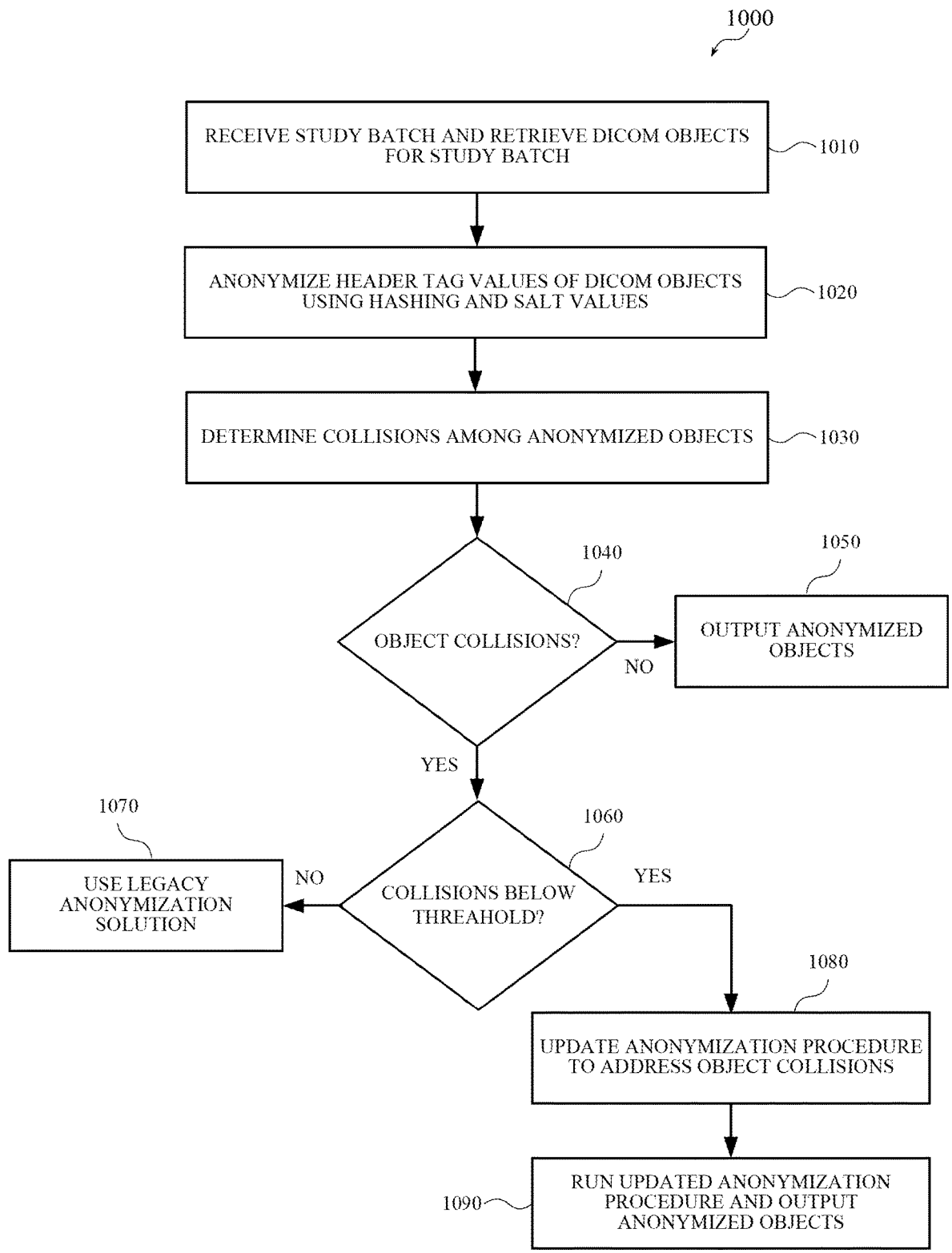
FIG. 10 is a diagram of an example process for determining how to de-identify a batch of DICOM objects based on an analysis of collisions between DICOM records according to one or more implementations described herein.

FIG. 10 is a diagram of an example process 1000 for determining how to de-identify a batch of DICOM objects based on an analysis of collisions between DICOM records according to one or more implementations described herein. Process 1000 may be implemented by one or more DICOM servers 220. In some implementations, some or all of process 1000 may be performed by one or more other systems or devices, including one or more of the devices of FIG. 2. Additionally, process 1000 may include one or more fewer, additional, differently ordered and/or arranged operations than those shown in FIG. 10 and may be implemented within the context of a variety of other processes involving different devices. For example, in some implementations, process 1000 may include checking for collisions before anonymizing DICOM records instead or, or in addition to, doing so afterwards.

In some implementations, some or all of the operations of process 1000 may be performed independently, successively, simultaneously, etc., of one or more of the other operations of process 1000. For example, process 1000 may involve include DICOM servers 220 receiving commands or other types of inputs from UE 210, performing one or more operations of process 1000, and providing UE 210 with corresponding results or outputs. In some implementations, process 1000 may involve include UE 210 requesting and receiving a DICOM study batch from DICOM servers 220, UE 210 anonymizing certain header tags of the DICOM study batch and providing the anonymized DICOM study batch to DICOM servers 220 and/or to another type of computing device, such as DICOM sources/destinations 250.

In some implementations, DICOM sources/destinations 250 may send a request to UE 210 for an anonymized DICOM study batch, UE 210 may communicate with DICOM servers 220 to access (from data repository 230) the DICOM study batch and to anonymize the DICOM study batch and inform DICOM sources/destinations 250 when the anonymization is complete so that DICOM sources/destinations 250 may retrieve the anonymized DICOM study batch from DICOM servers 220. As such, the techniques described herein are not limited to a number, sequence, arrangement, timing, etc., of the operations or process depicted in FIG. 10.

As shown, process 1000 may include receiving a study batch and retrieving DICOM objects for the study batch (block 1010). For example, DICOM servers 220 may receive a request from UE 210 to anonymize a DICOM study batch that includes one or more DICOM objects (also referred to as DICOM records, DICOM instances, etc.). The request for the DICOM study batch may indicate the DICOM objects included in the study. This may be done based on one or more parameters, or combinations of parameters, such as DICOM objects between certain date ranges, associated with a particular hospital or other institution, one or more patient attributes (e.g., name, age, gender, city, state, etc.), one or more type of image data (e.g., x-ray, magnetic resonance imaging (MRI) scan, etc.), one or more DICOM object UIs, etc. DICOM servers 220 may retrieve the DICOM objects for the study, based on the request, from data repository 230.

Process 1000 may also include anonymizing header tag values of DICOM objects using hashing algorithms and salt values (block 1020). For example, DICOM servers 220 may identify target tags in headers of the DICOM objects and anonymize the values corresponding to the tags by apply one or more hashing algorithms and salt values. In some implementations, anonymization rules or instructions may be applied such that only certain tags, or certain types of tags, may be anonymized. In some implementations, different hashing functions may be used for different types of types of header tags. Additionally, or alternatively, a different or unique salt value may be used for each type of hashing function and/or study batch. The instructions may be received or selected by UE 210. Alternatively, the instructions may be identified by DICOM servers 220 based on another condition, such as a type, quantity, category, etc., of the DICOM objects, a stated purpose for the record request, a user, institution, or organization indicated as requesting the DICOM study batch, etc. In some implementations, DICOM servers 220 may be configured to anonymize one or more types of header tags, such as identification tags, unique identification tags, etc.

DICOM servers 220 may obtain the requested DICOM objects, determine which types of tags are to be anonymized, identify the tags in each DICOM object header, and proceed to anonymize the value of the identified tags. This may include DICOM servers 220 using the value of the tag (or a combination or concatenation of the value of several tags) as an input to one or more hashing functions and salt values to produce a corresponding output that is unique yet anonymizes the input value. As DICOM servers 220 may use the same hashing function and salt value to anonymize the same type of tag (e.g., patient name) for each DICOM object of the DICOM study batch, DICOM servers 220 may not be encumbered by storing a record of which input value was linked to which output value since the same hashing function and salt value will ensure that the same input value results in the same output value. In this manner, the data integrity and consistency between DICOM objects may be preserved.

Process 1000 may include determining and resolving collisions among anonymized DICOM objects (block 1030). For example, DICOM servers 220 may analyze a batch of DICOM studies to determine whether there are collisions between anonymized DICOM objects. In some implementations, DICOM servers 220 may also, or alternatively, analyze a batch of DICOM studies and/or objects prior to anonymizing header tag values of DICOM objects. In some implementations, this may help ensure that taking the time and resources to perform an entire anonymization procedure would not result in any collisions or would only result in a manageable number of collisions.

A collision may include a scenario in which anonymized tag values (e.g., a patient ID) for different DICOM objects (e.g., from different DICOM studies) end up being the same when they should be different, and therefore create confusion as to which DICOM objects pertain to which DICOM objects, studies, batches, etc. For example, if different people went to different hospitals but ended up having the same patient IDs, a collision may arise if the patient IDs were each input into the same hashing function because it would result in the same output value and therefore make it appear as though each DICOM object corresponds to the same person even though they do not.

When no collisions are detected (block 1040—No), process 1000 may include outputting anonymized DICOM objects for the study batch (block 1050). For example, DICOM servers 220 may produce the anonymized DICOM objects of the study batch. In some implementations, this may include sending a message, posting a link, creating and hosting a file structure, etc., to enable another device to access and download the anonymized DICOM objects. In some implementations, this may also, or alternatively, including storing the anonymized DICOM objects as a study batch in data repository 230, a VNA, or another location.

When a collisions are detected (block 1040—Yes), process 1000 may include determining whether the number of collisions exceeds a collision threshold number (block 1060) When the threshold is exceeded (block 1060—Yes) process 1000 may proceed by anonymizing the study batch using legacy anonymization techniques (block 1070). For example, DICOM servers 220 may de-identify the study batch by using processes that creates an index of all anonymized UIs during the anonymization process, maintains the UIs in memory as each UI is created and used, and periodically refers back to the index to determine when an existing anonymized UI should be used for a particular tag value or whether a new anonymized UI should be used for a particular tag value. When the threshold is not exceeded (block 1060—No) process 1000 may proceed by resolving the collisions among the anonymized objects (block 1080). For example, DICOM servers 220 may resolve collisions by implementing one or more rules pre-emptively (before anonymizing header tags) and/or retroactively (after anonymizing header tags). Retroactively resolving collisions may include rolling back the anonymization of one or more header tag values, modifying an input value, a salt value, etc., and reapplying the hash functions to produce a corrective output.

In some implementations, DICOM servers 220 may resolve a collision by adding, editing, or deleting one or more portions of the value of a tag prior to anonymization processing. For example, in a scenario where a DICOM batch includes studies from multiple institutions, it may be possible that applying the same hashing functions and salt values to a particular tag type for all objects in the batch could create collisions. As such, DICOM servers 220 may be configured to add, edit, or delete information from the input or the output of a hashing function. For example, assume the for objects pertaining to Institution ABC, DICOM servers 220 may add the letters ABC to hashing function input (e.g., add the prefix "ABC" to each patient name) so that all of the outputs from the objects pertaining to Institution ABC are distinguishable from the outputs of another research institution (e.g., Institution XYZ). That is, the output for the patient name "Brian" of Institution ABC will be different than the output for "Brian" of Institution XYZ because the hashing function input for "Brian" of Institution ABC would be "ABCBrian" while for "Brian" of Institution XYZ may be "Brian" or perhaps "XYZBrian." In this manner, DICOM servers 220 may avoid collisions and confusion, but still achieve anonymization and inter-record consistency, by modifying hashing function inputs.

Process 1000 may include outputting anonymized DICOM objects for the study batch (block 1090). For example, DICOM servers 220 may produce the anonymized DICOM objects of the study batch. In some implementations, this may include sending a message, posting a link, creating and hosting a file structure, etc., to enable another device to access and download the anonymized DICOM objects. In some implementations, this may also, or alternatively, including storing the anonymized DICOM objects as a study batch in data repository 230, a VNA, or another location.

Figure 11:
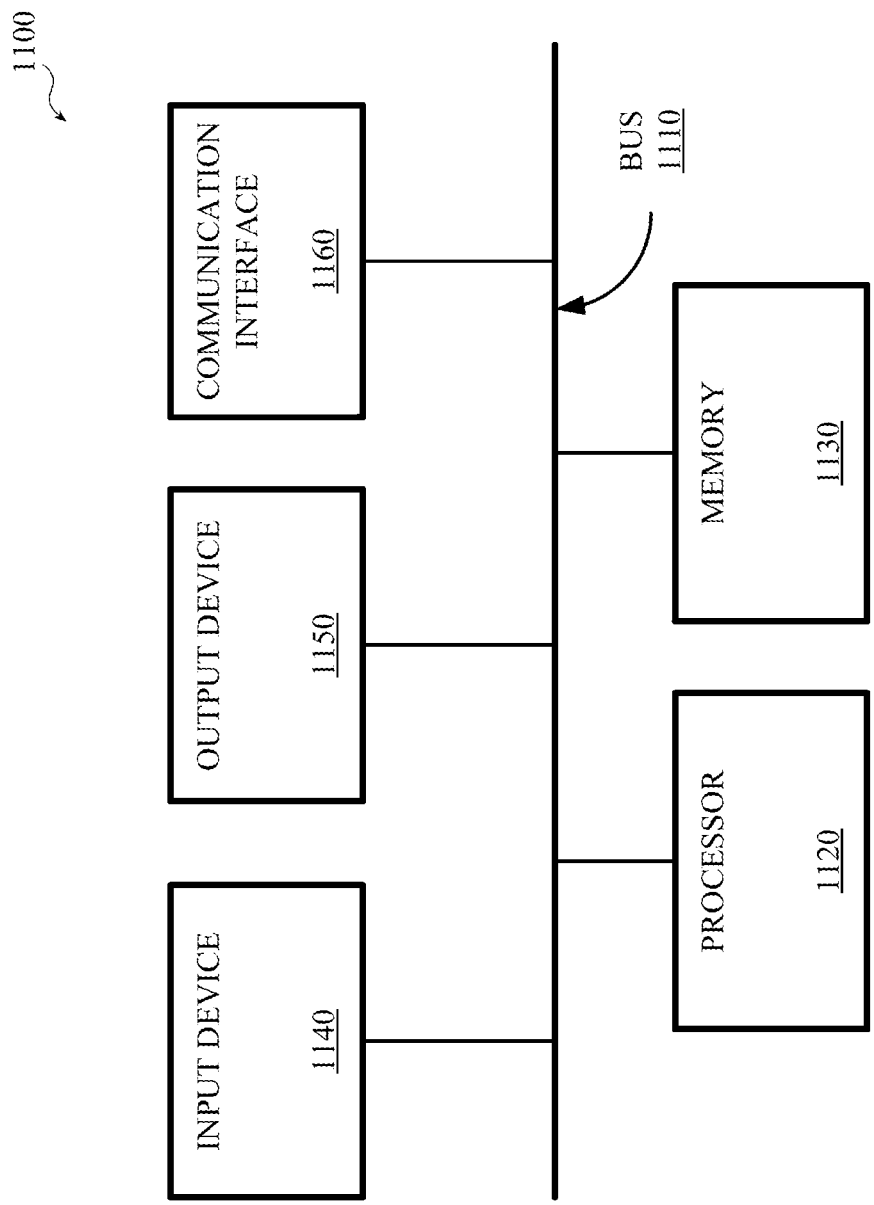
FIG. 11 is a diagram of example components of a device that may be used within environment of FIG. 2.

FIG. 11 is a diagram of example components of a device 1100 that may be used within environment 200 of FIG. 2. Device 1100 may correspond to UE 210, DICOM servers 220, data repository 230, platform management terminal 240, and/or DICOM information source/destination 260.

Each of UE 210, DICOM servers 220, data repository 230, platform management terminal 240, and/or DICOM information source/destination 260 may include one or more of devices 1100 and/or one or more of the components of device 1100.

As depicted, device 1100 may include bus 1110, processor 1120, memory 1130, input device 1140, output device 1150, and communication interface 1160. However, the precise components of device 1100 may vary between implementations. For example, depending on the implementation, device 1100 may include fewer components, additional components, different components, or differently arranged components than those illustrated in FIG. 11.

Bus 1110 may permit communication among the components of device 1100. Processor 1120 may include one or more processors, microprocessors, data processors, co-processors, network processors, application-specific integrated circuits (ASICs), controllers, programmable logic devices (PLDs), chipsets, field-programmable gate arrays (FPGAs), or other components that may interpret or execute instructions or data. Processor 1120 may control the overall operation, or a portion thereof, of device 1100, based on, for example, an operating system (not illustrated), and/or various applications. Processor 1120 may access instructions from memory 1130, from other components of device 1100, or from a source external to device 1100 (e.g., a network or another device).

Memory 1130 may include memory and/or secondary storage. For example, memory 1130 may include random access memory (RAM), dynamic RAM (DRAM), read-only memory (ROM), programmable ROM (PROM), flash memory, or some other type of memory. Memory 1130 may include a hard disk (e.g., a magnetic disk, an optical disk, a magneto-optic disk, a solid state disk, etc.) or some other type of computer-readable medium, along with a corresponding drive. A computer-readable medium may be defined as a non-transitory memory device. A memory device may include space within a single physical memory device or spread across multiple physical memory devices.

Input device 1140 may include one or more components that permit a user to input information into device 1100. For example, input device 1140 may include a keypad, a button, a switch, a knob, fingerprint recognition logic, retinal scan logic, a web cam, voice recognition logic, a touchpad, an input port, a microphone, a display, or some other type of input component. Output device 1150 may include one or more components that permit device 1100 to output information to a user. For example, output device 1150 may include a display, light-emitting diodes (LEDs), an output port, a speaker, or some other type of output component.

Communication interface 1160 may include one or more components that permit device 1100 to communicate with other devices or networks. For example, communication interface 1160 may include some type of wireless or wired interface. Communication interface 1160 may also include an antenna (or a set of antennas) that permit wireless communication, such as the transmission and reception of radio frequency (RF) signals.

As described herein, device 1100 may perform certain operations in response to processor 1120 executing software instructions contained in a computer-readable medium, such as memory 1130. The software instructions may be read into memory 1130 from another computer-readable medium or from another device via communication interface 1160. The software instructions contained in memory 1130 may cause processor 1120 to perform one or more processes described herein. Alternatively, hardwired circuitry may be used in place of, or in combination with, software instructions to implement processes described herein. Thus, implementations described herein are not limited to any specific combination of hardware circuitry and software.

Examples herein can include subject matter such as a method, means for performing acts or blocks of the method, at least one machine-readable medium including executable instructions that, when performed by a machine (e.g., a processor (e.g., processor, etc.) with memory, an application-specific integrated circuit (ASIC), a field programmable gate array (FPGA), or the like) cause the machine to perform acts of the method or of an apparatus or system for concurrent communication using multiple communication technologies according to implementations and examples described.

In example 1, which may also include one or more of the example described herein, a server device, may comprise: a memory; and one or more processors configured, when executing instructions stored in the memory, to: receive a request to anonymize one or more digital imaging and communications in medicine (DICOM) objects; create, based on the one or more DICOM objects, anonymized DICOM objects by using one or more hashing algorithms to anonymize identifying information of the one or more DICOM objects; and output, in response to the request, the anonymized DICOM objects.

In example 2, which may also include one or more of the example described herein, wherein each DICOM object of the one or more DICOM objects comprises a header portion and an image portion. In example 3, which may also include one or more of the example described herein, wherein each anonymized DICOM object, of the anonymized DICOM objects, comprises at least one anonymized header tag value changed from a header tag value containing identifying information. In example 4, which may also include one or more of the example described herein, wherein each anonymized DICOM object, of the anonymized DICOM objects, comprises an anonymized header portion and an unchanged image portion.

In example 5, which may also include one or more of the example described herein, wherein the one or more processors are further configured to: analyze the anonymized DICOM objects for collisions between the anonymized DICOM objects. In example 6, which may also include one or more of the example described herein, wherein the one or more processors are further configured to: resolve collisions between the anonymized DICOM objects. In example 7, which may also include one or more of the example described herein, wherein resolving collisions between anonymized DICOM objects comprises modifying hashing function inputs upon which the collisions are based.

In example 8, which may also include one or more of the example described herein, a method, performed by a server device, may comprise: receiving a request to anonymize one or more digital imaging and communications in medicine (DICOM) objects; creating, based on the one or more DICOM objects, anonymized DICOM objects by using one or more hashing algorithms to anonymize identifying information of the one or more DICOM objects; and outputting, in response to the request, the anonymized DICOM objects.

In example 9, which may also include one or more of the example described herein, a non-transitory computer-readable medium may comprise: instructions that when executed by one or more processors, cause the one or more processors to: receive a request to anonymize one or more digital imaging and communications in medicine (DICOM) objects; create, based on the one or more DICOM objects, anonymized DICOM objects by using one or more hashing algorithms to anonymize identifying information of the one or more DICOM objects; and output, in response to the request, the anonymized DICOM objects.

The above description of illustrated examples, implementations, aspects, etc., of the subject disclosure, including what is described in the Abstract, is not intended to be exhaustive or to limit the disclosed aspects to the precise forms disclosed. While specific examples, implementations, aspects, etc., are described herein for illustrative purposes, various modifications are possible that are considered within the scope of such examples, implementations, aspects, etc., as those skilled in the relevant art can recognize.

In this regard, while the disclosed subject matter has been described in connection with various examples, implementations, aspects, etc., and corresponding Figures, where applicable, it is to be understood that other similar aspects can be used or modifications and additions can be made to the disclosed subject matter for performing the same, similar, alternative, or substitute function of the subject matter without deviating therefrom. Therefore, the disclosed subject matter should not be limited to any single example, implementation, or aspect described herein, but rather should be construed in breadth and scope in accordance with the appended claims below.

In particular regard to the various functions performed by the above described components or structures (assemblies, devices, circuits, systems, etc.), the terms (including a reference to a "means") used to describe such components are intended to correspond, unless otherwise indicated, to any component or structure which performs the specified function of the described component (e.g., that is functionally equivalent), even though not structurally equivalent to the disclosed structure which performs the function in the herein illustrated exemplary implementations. In addition, while a particular feature may have been disclosed with respect to only one of several implementations, such feature may be combined with one or more other features of the other implementations as may be desired and advantageous for any given application.

As used herein, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form. Furthermore, to the extent that the terms "including", "includes", "having", "has", "with", or variants thereof are used in either the detailed description or the claims, such terms are intended to be inclusive in a manner similar to the term "comprising." Additionally, in situations wherein one or more numbered items are discussed (e.g., a "first X", a "second X", etc.), in general the one or more numbered items can be distinct, or they can be the same, although in some situations the context may indicate that they are distinct or that they are the same.

It is well understood that the use of personally identifiable information should follow privacy policies and practices that are generally recognized as meeting or exceeding industry or governmental requirements for maintaining the privacy of users. In particular, personally identifiable information data should be managed and handled to minimize risks of unintentional or unauthorized access or use, and the nature of authorized use should be clearly indicated to users.

What is claimed is:

1. A server device, comprising:
   a memory; and
   one or more processors configured, when executing instructions stored in the memory, to:
      receive a request to anonymize one or more digital imaging and communications in medicine (DICOM) objects;
      create, based on the one or more DICOM objects, anonymized DICOM objects by using one or more hashing algorithms to anonymize identifying information of the one or more DICOM objects; and
      output, in response to the request, the anonymized DICOM objects.

2. The server device of claim 1, wherein each DICOM object of the one or more DICOM objects comprises a header portion and an image portion.

3. The server device of claim 2, wherein each anonymized DICOM object, of the anonymized DICOM objects, comprises at least one anonymized header tag value changed from a header tag value containing identifying information.

4. The server device of claim 2, wherein each anonymized DICOM object, of the anonymized DICOM objects, comprises an anonymized header portion and an unchanged image portion.

5. The server device of claim 1, wherein the one or more processors are further configured to:
   analyze the anonymized DICOM objects for collisions between the anonymized DICOM objects.

6. The server device of claim 5, wherein the one or more processors are further configured to:
   resolve collisions between the anonymized DICOM objects.

7. The server device of claim 6, wherein resolving collisions between anonymized DICOM objects comprises modifying hashing function inputs upon which the collisions are based.

8. A method, performed by a server device, comprising:
   receiving a request to anonymize one or more digital imaging and communications in medicine (DICOM) objects;
   creating, based on the one or more DICOM objects, anonymized DICOM objects by using one or more hashing algorithms to anonymize identifying information of the one or more DICOM objects; and
   outputting, in response to the request, the anonymized DICOM objects.

9. The method of claim 8, wherein each DICOM object of the one or more DICOM objects comprises a header portion and an image portion.

10. The method of claim 9, wherein each anonymized DICOM object, of the anonymized DICOM objects, comprises at least one anonymized header tag value changed from a header tag value containing identifying information.

11. The method of claim 9, wherein each anonymized DICOM object, of the anonymized DICOM objects, comprises an anonymized header portion and an unchanged image portion.

12. The method of claim 8, further comprising:
   analyzing the anonymized DICOM objects for collisions between the anonymized DICOM objects.

13. The method of claim 12, further comprising:
   resolving collisions between the anonymized DICOM objects.

14. The method of claim 13, wherein resolving collisions between anonymized DICOM objects comprises modifying hashing function inputs upon which the collisions are based.

15. A non-transitory computer-readable medium comprising:
instructions that when executed by one or more processors, cause the one or more processors to:
receive a request to anonymize one or more digital imaging and communications in medicine (DICOM) objects;
create, based on the one or more DICOM objects, anonymized DICOM objects by using one or more hashing algorithms to anonymize identifying information of the one or more DICOM objects; and
output, in response to the request, the anonymized DICOM objects.

16. The non-transitory computer-readable medium of claim 15, wherein each DICOM object of the one or more DICOM objects comprises a header portion and an image portion.

17. The non-transitory computer-readable medium of claim 16, wherein each anonymized DICOM object, of the anonymized DICOM objects, comprises at least one anonymized header tag value changed from a header tag value containing identifying information.

18. The non-transitory computer-readable medium of claim 16, wherein each anonymized DICOM object, of the anonymized DICOM objects, comprises an anonymized header portion and an unchanged image portion.

19. The non-transitory computer-readable medium of claim 15, wherein the one or more processors are further configured to:
analyze the anonymized DICOM objects for collisions between the anonymized DICOM objects.

20. The non-transitory computer-readable medium of claim 19, wherein the one or more processors are further to:
resolve collisions between the anonymized DICOM objects.

* * * * *